United States Patent

Tafesh et al.

Patent Number: 6,008,387

Date of Patent: Dec. 28, 1999

[54] PROCESS FOR THE OXIDATION OF ORGANIC COMPOUNDS IN THE PRESENCE OF BIS- AND TRIS- ($\mu$-OXO)-DIMANGANESE COMPLEX SALTS AS CATALYST

[75] Inventors: Ahmed Tafesh, Corpus Christi, Tex.; Matthias Beller, Garching, Germany

[73] Assignee: Hoechst Aktiengesellschaft, Frankfurt, Germany

[21] Appl. No.: 08/778,295

[22] Filed: Jan. 2, 1997

[30] Foreign Application Priority Data

Jan. 4, 1996 [DE] Germany ............... 196 00 160

[51] Int. Cl.⁶ ..................................... C07D 301/12
[52] U.S. Cl. ........................................... 549/531
[58] Field of Search ............................... 549/531

[56] References Cited

FOREIGN PATENT DOCUMENTS

| | | |
|---|---|---|
| 0458397 | 11/1991 | European Pat. Off. |
| 0458398 | 11/1991 | European Pat. Off. |
| 0544519 | 6/1993 | European Pat. Off. |
| WO 93/25562 | 12/1993 | WIPO |

OTHER PUBLICATIONS

M. Sato et al., Synthesis, 1992, p. 539.
R. Hage et al., Nature, vol. 369, 1994, p. 637.
J. Glerup et al., Inorg. Chem. vol. 33, 1994, p. 4105.
M. Delroisse et al., J. Chem. Soc., Chem. Commun., 1995, p. 949.
P.A. Goodson et al., Inorg. Chem., vol. 28, 1989, p. 3606.
G.A. McLachlan et al., Inorg. Chem., vol. 33, 1994, p. 4663.
S.R. Cooper et al., of the Am. Chem. Soc., 1977, p. 6623.
K. Weighardt et al., J. Am. Chem. Soc., vol. 110, No. 22, 1988, P. 7398.
G. Christou, Acc. Chem. Res., vol. 22, No. 9, 1989.
Tetrahedron Letters, Bd. 36, No. 31, 1995, Oxford, GB, pp. 5457–5460, XP002029299 by M. Palucki et al.

*Primary Examiner*—Ba K. Trinh
*Attorney, Agent, or Firm*—Frommer Lawrence & Haug LLP

[57] ABSTRACT

Disclosed and claimed are oxidation reactions involving, as a catalyst, a bis- and/or tris-($\mu$-oxo)-dimanganese complex salt of the formula I $$[LMn(\mu\text{-O})_a(\mu\text{-OAc})_b MnL]^x A_y \qquad (I)$$

Ac is a $C_2$–$C_8$-acyl group, a is 1, 2 or 3, b is 0 when a is 2 or 3 or b is 2 when a is 1, x indicates the number of positive charges and is 2 or 3, A is a singly or doubly negatively charged anion, y is the number of anions A required to balance the positive charges and L is a ligand, such as N,N-bis(2-pyridylmethyl)-N-methylamine or N,N,N',N'-tetrakis(2-pyridyl(methyl)-N-methylamine or $N_1$ $N_1$ $N_1$, $N^1$-tetrakis(2-pyridylmethyl)-1,2-ethylenediamine.

10 Claims, No Drawings

PROCESS FOR THE OXIDATION OF ORGANIC COMPOUNDS IN THE PRESENCE OF BIS- AND TRIS- (µ-OXO)-DIMANGANESE COMPLEX SALTS AS CATALYST

RELATED APPLICATIONS

Reference is made to German applications 19600161.7 and 19600160.9, both filed Jan. 4, 1996; and to co-pending U.S. application Ser. No. 08/778,302, concurrently filed herewith. Each of these applications is incorporated herein by reference. In addition, documents cited throughout the following text are incorporated herein by reference.

FIELD OF THE INVENTION

This invention relates to processes for the oxidation of organic compounds comprising undertaking the oxidation in the presence of a bis- and/or tris-(µ-oxo)-dimanganese complex salt of the formula I (below), as a catalyst. That is, the invention relates to a process for oxidizing at least one organic compound comprising contacting the compound with the salt of formula I under oxidative conditions, whereby the salt of formula I catalyzes oxidation of the compound.

BACKGROUND OF THE INVENTION

A series of bis- and tris-(µ-oxo)-dimanganese complex salts have already been described, for example in WO 93/25562; Inorg. Chem. 1989, 28, p. 3606–3608; J. Chem. Soc. Chem. Comm. 1995, p. 949–950; Inorg. Chem. 1994, 33, 4105–4111 and Nature, Vol. 369, p. 637–639. Manganese complex salts of this type are also described in EP-A-0 458 397; EP-A-0 458 398 and EP-A-0 544 519. These manganese complex salts can serve as catalysts for oxidative bleaches. These manganese complex salts contain a ligand of the triazacyclononane type. This ligand and accordingly the prior manganese complex salts can only be prepared in a multistage process and are thus difficult and costly to obtain and use.

It would be a significant advance over the state of the art if new manganese salts, useful as catalysts, are provided, having more readily available ligands such that the salts are less difficult and costly to obtain and use and thus provide advantages, such as industrial advantages, over the prior manganese complex salts.

SUMMARY OF THE INVENTION

It has now surprisingly been found that there are new and nonobvious manganese complex salts (i.e., salts which have not previously been described or suggested) which are likewise very suitable as catalysts for oxidation reactions but which surprisingly contain more readily available ligands, and thus provide significant advantages over prior manganese complex salts.

The invention provides a process for the oxidation of an organic compound, preferably an organic compound having at least one electron dense bond, e.g., at least one double or triple carbon-carbon bond, for instance, a vinyl or styrene compound. The process comprises carrying out the oxidation in the presence of a bis- and/or tris-(µ-oxo)-dimanganese complex salt comprised of the formula I, as a catalyst.

$$[LMn(\mu\text{-O})_a(\mu\text{-OAc})_b MnL]^x A_y \quad (I)$$

where

Ac is a $C_2$–$C_8$-acyl group, a is 1, 2 or 3, b is 0 when a is 2 or 3 or b is 2 when a is 1, x indicates the number of positive charges and is 2 or 3, A is a singly or doubly negatively charged anion, y is the number of anions A required to balance the positive charges and L is a ligand of the formula II or III

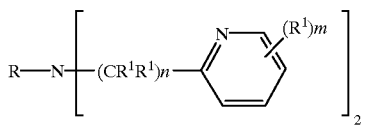

(II)

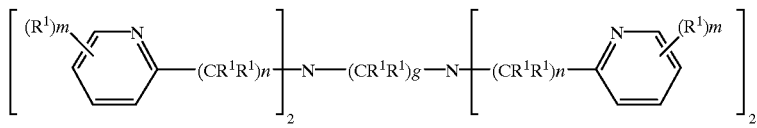

(III)

where R is $C_1$–$C_{12}$-alkyl, $C_5$–$C_{10}$-cycloalkyl, phenyl, $NH_2$, $NHR^2$, $N(R^2)_2$, OH, $OR^2$, or COOH, $R^1$ is hydrogen, $C_1$–$C_{12}$-alkyl, $C_5$–$C_{10}$-cycloalkyl, $NH_2$, $NHR_2$, $N(R^2)_2$, OH, $OR^2$, COOH, $COOR^2$, Cl, Br, F, I or CN, $R^2$ is $C_1$–$C_{12}$-alkyl or $C_5$–$C_{10}$-cycloalkyl, g is 2 or 3 and m and n are zero or an integer from 1 to 4.

DETAILED DESCRIPTION

Thus, the invention relates to an oxidation reaction of an organic compound performed in the presence of a formula I salt, as the catalyst.

Preferred salts of the formula I are those in which substituents $R^1$ are hydrogen and n=1. When a=3 and b=0, L is preferably a ligand of the formula II. Preferred salts of the formula I are also those in which a=1 and b=2 and L is a ligand of the formula III. In the case of salts of the formula I in which L is a ligand of the formula II, R is preferably $C_1$–$C_4$-alkyl, more preferably methyl. Suitable anions A are $F^-$, $Cl^-$, $Br^-$, $I^-$, $NO_3^-$, $ClO_4^-$, $NCS^-$, $PF_6^-$, $RSO_3^-$, $RSO_4^-$, $SO_4^{2-}$, $BPh_4^-$, and also anions of organic compounds, e.g., aliphatic and aromatic alcohols and carboxylic acids such as tosylate, acetate and benzoate. In general as to anions compounds such as aliphatic and aromatic carboxylic acids, reference is made to Streitweiser & Heathcock, Introduction to Organic Chemistry (1976), e.g., Chapter 17, App. IV; any of the anions disclosed therein can be used in the invention. Preferred anions are $PF_6^-$, $ClO_4^-$, tosylate, acetate and benzoate.

The ligands of the formula III present in the manganese complex salts of the invention are prepared, for example, by reacting 2-(chloromethyl)-pyridinium chloride with ethylenediamine in the presence of a phase transfer catalyst (see Synthesis, June 1992, pp. 539–540) or in an analogous manner for the substituted other ligands of the formula III. In a similar manner, the ligands of the formula II are prepared by reacting 2-(chloromethyl)pyridinium chloride or analogous pyridinium compounds with an amine $R-NH_2$. The manganese complex salts of the invention having the formula I are prepared by the method described in Inorg. Chem. 1989, 28, 3606–3608, by oxidizing an aqueous solution containing $MnCl_2$ and the ligand with $H_2O_2$ or by a method similar to the process described in Inorg. Chem. 1994, 33, 4105–4111, in which the oxidation is carried out using ammonium peroxodisulfate.

Accordingly, the method for preparing a formula I salt can comprise oxidizing a solution containing $Mn^{2+}$ and L. The oxidizing can be with a peroxide or peroxidisulfate, and the peroxide can be $H_2O_2$ or the peroxidisulfate can be ammonium peroxodisulfate. The solution can be an aqueous solution. And, the $Mn^{2+}$ can be in the form of MnAy, such as $MnCl_2$.

According to the invention, the resulting manganese complex salts of the formula I are used as catalysts for the oxidation of organic compounds. The organic compounds in the oxidation reaction may be any organic compounds; however, compounds having at least one electron dense bond, e.g., at least one double or triple carbon-carbon bond are preferred; for instance, at least one unsaturated bond, such as an alkene or alkyne. More preferably, the reaction employing the formula I salt is an oxidation of a vinyl compound of the formula $R-CH=CH_2$, where R is an aromatic radical, preferably phenyl, or $C_1-C_{10}$-alkyl, which may be unsubstituted or substituted, e.g., by a halogen such as F, Cl, I, Br, OH, $OR^2$, CN, $NH_2$, $NHR^2$, $N(R^2)$ (where $R^2$ is as defined above), or the like. Thus, the organic compound to be oxidized in the presence of the formula I salt as a catalyst can be a styrene or substituted styrene.

The following non-limiting examples are given by way of illustration only and are not to be considered a limitation of this invention.

PREPARATIVE EXAMPLES

Example 1

Tris-($\mu$-oxo)-bis[N,N-bis(2-pyridylmethyl)-N-methylamine]dimanganese(IV, IV) hexafluorophosphate 1.74 g (8.8 mmol) of $MnCl_2.4H_2O$, 1.88 g (8.8 mmol) of N,N-bis(2-pyridylmethyl)-N-methylamine and 1.75 g (9.5 mmol) of $KPF_6$ were dissolved in 600 ml of a mixture of ethanol and water (2:1). The solution was stirred for 20 minutes at room temperature and then cooled in an ice bath to 5° C. 10 ml of $H_2O_2$ (3% strength) and 2.6 ml of a 20% strength aqueous NaOH solution were added, with the temperature rising to 10° C. and a precipitate being formed. This mixture was stirred for 1 hour at 5° C. and one further hour at 20° C. The precipitate was filtered off and washed with water. Crude yield: 6.1 g. After drying, the solid was treated with acetone to leave $MnO_2$ as solid. The acetone solution was filtered from the insoluble $MnO_2$ and the acetone was distilled off. This gave 1.25 g of a gray-green solid.

Analysis

| calc.: | C 40.9% H 3.8% N 10.9% |
|---|---|
| found: | C 39.5% H 3.6% N 10.4% |

Example 2

Tris-($\mu$-oxo)-bis[N,N,N',N'-tetrakis(2-pyridylmethyl)-1,2-ethylenediamine]dimanganese (IV,IV) hexafluorophosphate A mixture of 25.5 ml of ethanol and 4.5 ml of water was degassed by applying a vacuum three times and was then treated with argon in order to remove all residual oxygen which would otherwise oxidize Mn(II) to Mn(IV). To this mixture was added 2.47 g (5.82 mmol) of N,N,N',N'-tetrakis (2-pyridylmethyl)ethylenediamine. This gave a yellow solution having a pH of 8.8. 0.96 g (3.6 mmol) of manganese triacetate $(Mn(OAc)_3.3H_2O)$ was then added. The solution became brown and had a pH of 6.2. Subsequently, 2 g (14.58 mmol) of sodium acetate was added (pH 6.5), then perchloric acid (55 drops) to a pH of 5 was added. After addition of 3 g (24.48 mmol) of sodium perchlorate, a precipitate was formed at pH 6.1. This reaction mixture was left for 4 hours. The precipitated crystals were filtered off under nitrogen. This gave 3.08 g of crude product of the compound ($\mu$-oxo)-bis-($\mu$-acetato)-bis[N,N,N',N'-(2-pyridylmethyl) ethylenediamine]dimanganese-(III,III) perchlorate.

1.15 g (0.823 mmol) of this compound was dissolved in 40 ml of a 1:1 mixture of ethanol and water. After half an hour, 4 ml of triethylamine was added. The pH of the reaction mixture was 11. 3.89 g (21.12 mmol) of $KPF_6$ was then added. After 15 minutes, the reaction mixture was filtered to remove insoluble manganese dioxide. The solvent was distilled from the filtrate and the residue was treated with acetone in order to remove residual amounts of manganese dioxide, since the desired complex salt is readily soluble in acetone, unlike manganese dioxide. After separating off the manganese dioxide, the acetone was removed by distillation. This gave the title compound in the form of a white powder.

Example 3

($\mu$-Oxo)-bis-($\mu$-butyrato)-bis[N,N,N',N'-tetrakis 2-pyridylmethyl)-1,2-ethylenediamine]dimanganese (III,IV) perchlorate 2.47 g (5.82 mmol) of N,N,N',N'-tetrakis(2-pyridylmethyl)-1,2-ethylenediamine was dissolved in 30 ml of a mixture of ethanol and water (5:1) and then Mn(OAc)$_3$.2H$_2$O (0.96 g; 3.6 mmol) was added thereto. Subsequently, 2.2 g (20 mmol) of sodium butyrate were added and then 2 ml of $HClO_4$ (70% strength). A pH of 7.5 was established. 3 g (24.48 mmol) of $NaClO_4$ was then added and this mixture was stirred for 4 hours at room temperature. A precipitate was formed and this was filtered off, washed with an ethanol/water mixture (85% of EtOH/15% of $H_2O$) and dried. Crude yield: 2.3 g. The solid was treated with 70 ml of acetone and the acetone solution was filtered from the insoluble inorganic salts. Distilling off the acetone and recrystallization from ethanol/water (5:1) gave the above-mentioned complex salt.

Analysis

| calc.: | Mn 7.5% C 49.17% H 4.95% N 11.47% |
|---|---|
| found: | Mn 8.0% C 44.8% H 4.5% N 12.1% |

Example 4

Bis-($\mu$-oxo)-bis[N,N,N',N'-tetrakis(2-pyridylmethyl)-1,2-ethylenediamine]dimanganese(III,IV) Perchlorate 0.425 g (1 mmol) of N,N,N',N'-tetrakis(2-pyridylmethyl)-1,2-ethylenediamine and 0.198 g (1 mmol) of $MnCl_2.4H_2O$ were dissolved in 6 ml of water. The solution was stirred for 30 minutes at room temperature. 4 drops of $H_2O_2$ were then added and the mixture was stirred for one hour at room temperature. Subsequently, 0.13 g (1 mmol) of $NaClO_4$ was added and the mixture was stirred for 3.5 hours at room temperature. The precipitated manganese complex salt was filtered off and washed with a 1 molar solution of $NaClO_4$ Analysis

| calc.: | Mn 8.4% C 47.77% H 4.47% Cl 8.14% N 12.86% |
|---|---|
| found: | Mn 8.4% C 45.1% H 4.3% Cl 8.6% N 11.9% |

The ligand N,N,N',N'-tetrakis(2-pyridylmethyl) ethylenediamine used in the above examples was prepared as described in Synthesis, 1992, p. 539.

Example 5

Bis-($\mu$-oxo)-bis[N,N,N',N'-tetrakis(2-pyridylmethyl)-1,2-ethylenediamine]dimanganese(III,IV) peroxodisulfate A mixture of 4.6 g (10.5 mmol) of N,N,N',N'-tetrakis-(2-pyridylmethyl)-1,2-ethylenediamine and 1.98 g of $MnCl_2$-$4H_2O$ was stirred for one hour in 15 ml (1.5 mmol) of 0.1 M HCl. The water was then distilled off and a solution of 7.5 g (32.8 mmol) of $(NH_4)_2SO_8$ in 20 ml of water was added. This mixture was stirred for one hour at room temperature. A precipitate was formed and this was filtered off and washed with water. Drying under reduced pressure gave 7.9 g of the crude product. This crude product was treated with 100 ml of acetone for 30 minutes. The manganese dioxide remaining as a solid was filtered off and the acetone solution was evaporated under reduced pressure. Drying under reduced pressure gave 6.30 g of the abovementioned manganese complex salt.

Analysis

| calc: | Mn 8.47%; C 48.15%; H 4.5%; N 12.96% |
|---|---|
| found: | Mn 8.1%; C 43.9%; H 3.7%; N 11.9%. |

USE EXAMPLES

Example 1
Oxidation of Styrene 0.0178 g (0.02 mmol) of the complex salt as described in Preparative Example 1 was added to a mixture of 0.208 g (2 mmol) of styrene in 20 ml of $CH_2Cl_2$ and 1.68 g (20 mmol) of sodium hydrogen carbonate in 20 ml of water. After a reaction time at room temperature of 10 minutes, 20 ml of $H_2O_2$ (30% strength) was added slowly over a period of 2.5 hours, with the temperature rising to 28° C. After a further 22 hours, the reaction was complete. The layers were separated and the organic phase was evaporated under reduced pressure. The product obtained was purified by column chromatography giving styrene oxide in a yield of 54% based on styrene.

Example 2
Oxidation of 3-chlorostyrene 2 mmol of 3-chlorostyrene in 20 ml of $CH_2Cl_2$ was oxidized in the presence of 0.0178 g (0.02 mmol) of the complex salt as described in Preparative Example 1 and 1.68 g (20 mmol) of sodium hydrogen carbonate using a method similar to that in Use Example 1. This gave 3-chlorostyrene oxide in a yield of 49% based on 3-chlorostyrene.

Example 3
Preparation of 1-chloro-2-phenylethanol from styrene 0.0178 g (0.02 mmol) of the complex salt described in Preparative Example 1 was added to a mixture of 0.208 g (2 mmol) of styrene in 20 ml of $CH_2Cl_2$ and 1.68 g (20 mmol) of sodium hydrogen carbonate in 20 ml of water. After a reaction time at room temperature of 10 minutes, 1.5 g (20 mmol) of NaOCl was added slowly over a period of 15 minutes, with the temperature rising to 28° C. After a further 6 hours, the reaction was complete. The layers were separated and the organic phase was evaporated under reduced pressure. The product obtained was purified by column chromatography. This gave 1-chloro-2-phenylethanol in a yield of 40% based on styrene.

Example 4
Preparation of Styrene Oxide

A mixture of 0.208 g of styrene (2 mmol) in 10 ml of $CH_2Cl_2$ and 1.68 g (20 mmol) of sodium hydrogen carbonate in 20 ml of water together with 0.026 g (0.02 mmol) of the complex salt described in Preparative Example 5 was stirred for 10 minutes at room temperature. 20 ml (200 mmol) of $H_2O_2$ (30% strength) was added slowly over a period of 2.5 hours, with the temperature rising to 28° C. The reaction mixture was stirred for a further 22 hours and the organic phase was then separated from the aqueous phase. The organic phase was evaporated under reduced pressure and the residue was purified by column chromatography. This gave styrene oxide in a yield of 49.6%.

Example 5
Preparation of Benzaldehyde

A mixture of 0.208 g of styrene in 2 ml of methanol and 40 ml of an aqueous solution of sodium carbonate was stirred together with 0.26 g (0.2 mmol) of the complex salt described in Preparative Example 5 for 10 minutes at room temperature. The amount of sodium carbonate was such that the pH of the reaction mixture was 6.5. 20 ml (200 mmol) of $H_2O_2$ (30% strength) was then added slowly over a period of 5 hours, with the temperature rising to 28° C. The reaction mixture was stirred for a further 24 hours and the aqueous phase was then separated from the organic phase. The organic phase was evaporated under reduced pressure and the residue was purified by column chromatography. This gave benzaldehyde in a yield of 48%.

Having thus described in detail preferred embodiments of the present invention, it is to be understood that the invention defined by the appended claims is not to be limited by particular details set forth in the above description as many apparent variations thereof are possible without departing from the spirit or scope thereof.

What is claimed is:

1. A process for the oxidation of an organic compound, which comprises contacting the organic compound with an oxidant under oxidation conditions in the presence of a bis- and/or tris-($\mu$-oxo)-dimanganese complex salt of the formula I

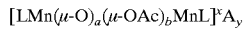

where

Ac is a $C_2$–$C_8$-acyl group, a is 1, 2 or 3, b is 0 when a is 2 or 3 or b is 2 when a is 1, x indicates the number of positive charges and is 2 or 3, A is a singly or doubly negatively charged anion, y is the number of anions A required to balance the positive charges and L is a ligand of the formula II or III

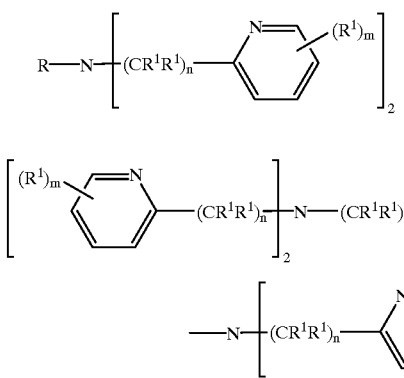

where R is $C_1$–$C_{12}$-alkyl, $C_5$–$C_{10}$-cycloalkyl, phenyl, $NH_2$, $NHR^2$, $N(R^2)_2$, OH, $OR^2$ or COOH, $R^1$ is hydrogen, $C_1$–$C_{12}$-alkyl, $C_5$–$C_{10}$-cycloalkyl, $NH_2$, $NHR^2$, $N(R^2)_2$, OH, $OR^2$, COOH, $COOR^2$, Cl, Br, F, I or CN, $R^2$ is $C_1$–$C_2$-alkyl or $C_5$–$C_{10}$-cycloalkyl, g is 2 or 3 and m and n are zero or an integer from 1 to 4.

2. The process as claimed in claim 1, wherein the oxidation is carried out in the presence of manganese complex salt of the formula I in which L is a ligand of the formula II or III in which $R^1$ is hydrogen.

3. The process as claimed in claim 1, wherein the oxidation is carried out in the presence of manganese complex salt of the formula I in which L is a ligand of the formula II in which R is $C_1$–$C_4$-alkyl.

4. The process as claimed in claim 1, wherein the organic compound comprises a vinyl compound of the formula

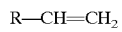

where R is an aromatic radical or $C_1$–$C_{10}$-alkyl.

5. The process as claimed in claim 1, wherein the organic compound comprises a styrene or a substituted styrene.

6. In a process for the oxidation of an organic compound, which comprises contacting the organic compound with an oxidant under oxidation conditions, wherein the improvement comprises carrying out the oxidation in the presence of a catalyst comprising a bis- and/or tris-($\mu$-oxo)-dimanganese complex salt of the formula I

where

Ac is a $C_2$–$C_8$-acyl group, a is 1, 2 or 3, b is 0 when a is 2 or 3 or b is 2 when a is 1, x indicates the number of positive charges and is 2 or 3, A is a singly or doubly negatively charged anion, y is the number of anions A required to balance the positive charges and L is a ligand of the formula II or III

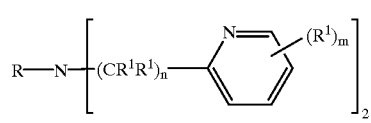

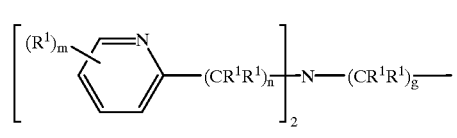

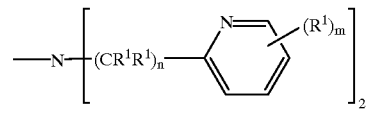

where R is $C_1$–$C_{12}$-alkyl, $C_5$–$C_{10}$-cycloalkyl, phenyl, $NH_2$, $NHR^2$, $N(R^2)_2$, OH, $OR^2$ or COOH, $R^1$ is hydrogen, $C_1$–$C_{12}$-alkyl, $C_5$–$C_{10}$-cycloalkyl, $NH_2$, $NHR^2$, $N(R^2)_2$, OH, $OR^2$, COOH, $COOR^2$, Cl, Br, F, I or CN, $R^2$ is $C_1$–$C_{12}$-alkyl or $C_5$–$C_{10}$-cycloalkyl, g is 2 or 3 and m and n are zero or an integer from 1 to 4.

7. The process as claimed in claim 6, wherein the oxidation is carried out in the presence of a catalyst comprising a manganese complex salt of the formula I in which L is a ligand of the formula II or III in which $R^1$ is hydrogen.

8. The process as claimed in claim 6, wherein the oxidation is carried out in the presence of a catalyst comprising a manganese complex salt of the formula I in which L is a ligand of the formula II in which R is $C_1$–$C_4$-alkyl.

9. The process as claimed in claim 6, wherein the organic compound comprises a vinyl compound of the formula

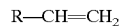

where R is an aromatic radical or $C_1$–$C_{10}$-alkyl.

10. The process as claimed in claim 1, wherein the organic compound comprises a styrene or a substituted styrene.

* * * * *